United States Patent [19]
Anastassiadis et al.

[11] Patent Number: 5,962,286
[45] Date of Patent: Oct. 5, 1999

[54] PROCESS FOR THE PRODUCTION OF GLUCONIC ACID WITH A STRAIN OF AUREOBASIDIUM PULLULANS (DE BARY) ARNAUD

[76] Inventors: Savas Anastassiadis, Artilleriestrasse 64; Alexander Aivasidis, Berliner Strasse 21; Christian Wandrey, Wolfshovener Strasse 139, all of P-5170 Jülich, Germany

[21] Appl. No.: 08/784,076

[22] Filed: Jan. 17, 1997

Related U.S. Application Data

[63] Continuation of application No. 08/069,202, May 28, 1993, abandoned.

[30] Foreign Application Priority Data

Jun. 1, 1992 [DE] Germany ............... 42 17 675

[51] Int. Cl.$^6$ ............... C12N 1/00; C12N 1/02; C12P 1/02; C12P 7/42
[52] U.S. Cl. ............ 435/146; 435/136; 435/169; 435/171; 435/255.1; 435/261; 435/822
[58] Field of Search ............... 435/146, 169, 435/171, 255.1, 822, 261, 136

[56] References Cited

U.S. PATENT DOCUMENTS

| | | | |
|---|---|---|---|
| 4,871,665 | 10/1989 | Viehweg | 435/104 |
| 5,681,732 | 10/1997 | De Graafl et al. | 435/197 |

FOREIGN PATENT DOCUMENTS 52010487  1/1977  Japan.

OTHER PUBLICATIONS

Su, Yuan–Chi et al., "Studies on Microbical Pred. of Sicl. Glucinate & Glucone–D–lacture from Stoids", 1977, pp. 143–160, See Abstract Only. Proc. Natl. Sci. Counc.

Ullmann's Encyclopaedia of Industrial Chemistry, 1989, vol. A12, pp. 449–455.

Perwoszwansky in Microbiology, Formation of Gluconic Acid During the Oxidation of Glucose by Bacteria, V.V. Perwoszandky, p. 149 1939.

*Primary Examiner*—David M. Naff
*Assistant Examiner*—Deborah K. Ware
*Attorney, Agent, or Firm*—Brenda Herschbach Jarrell; Sam Pasternack; Choate, Hall & Stewart

[57] ABSTRACT

Strains of *Aureobasidium pullulans* (de bary) Arnaud can be used for the commercial production of gluconic acid by fermentation in aqueous liquid containing sugar, which in continuous culture from glucose form greater than or equal to 90% and greater than or equal to 90% molar selectivity. The process is conducted with an Fe and Mn optimized medium with a nitrogen-independent (N-independent) ion concentration. The iron (Fe) concentration with 3 g/l $NH_4Cl$ is greater than or equal to 0.5 mM, and the manganese (Mn) concentration with 3 g/l $NH_4Cl$ is greater than or equal to about 0.5 mM manganese (Mn). The pH is regulated between about 4.5 and about 8, in particular at 6.5–7, and the temperature between 24 and 32° C., in particular at 29–30° C. Particularly successful strains are *Aureobasidium pullulans* (de bary) Arnaud with the registration numbers DSM 7085, DSM 7086, DSM 7087, and DSM 7088.

21 Claims, 9 Drawing Sheets

Fig. 1: Influence of pH on continuous formation of gluconic acid with Isolate No. 70 (5 mM Mn, 0.1 mM Fe, 3 g/l NH₄Cl)

Fig. 2: pH optimization in gluconic acid fermentation with Isolate No. 70
Specific productivity (BSP), Space-time yield (STY); 5 mM Mn, 100 µM Fe, So 270 g/l Fig 3: Influence of oxygen on continuous gluconic acid fermentation with Isolate No. 70 (DSM 7085)

Fig 4: Influence of oxygen on continuous gluconic acid fermentation with Isolate No. 70 (5 mM Mn, 0.5 mM Fe, pH 6.5, 30°C)

Fig. 5: Influence of oxygen on continuous gluconic acid fermentation with Isolate No. 70 (DSM 7085)

Fig. 6: Gluconic acid fermentation with Isolate No. 70 (DSM 7085) (X/D diagram: 0.5 mM Mn, 0.5 mM Fe, pH 6.4-6.5, So 249.63 g/l)

Fig. 7: STY (space-time yield) and specific productivity (BSP) as a function of the residence time (0.5 mM Mn, 0.5 mM Fe, pH 6.5, So 249-300 g/l)

Fig. 8: Continuous gluconic acid fermentation with Isolate No. 70 (DSM 7085); Manganese optimization in chemostat (100 µM Fe, 0.25–7.5 mM Mn)

Residence time much less than 20 h

Fig. 9: Continuous gluconic acid fermentation with Isolate No. 70 (DSM 7085); Manganese optimization in chemostat (100 μM Fe, 0.25–7.5 mM Mn)

Residence time much greater than 20 h

Fig. 10: Continuous gluconic acid fermentation with Isolate No. 70 (DSM 7085); Iron optimization in chemostat 5 mM Mn Residence time 12.4–12.9 h Fig. 11: Influence of iron on continuous gluconic acid fermentation with Isolate No. 70 (DSM 7085); (3 g/l NH₄Cl, 0.7 g/l KH₂PO₄, pH 6.5)

Fig. 12: Continuous gluconic acid fermentation with A. pullulans; Influence of iron (residence time ca. 13 h)

Fig. 13: Influence of iron on selectivity (5 mM Mn, pH 6.5, Retention time ca. 13 h)

Fig. 14: Influence of phosphorus on continuous gluconate fermentation (1.5 g/l NH₄Cl, 2.5 mM Mn, 0.25 mM Fe, pH 6.5)

Residence time ca. 13 h

Fig. 15: Influence of phosphorus on specific productivity and space-time yield (1.5 g/l NH$_4$Cl, 2.5 mM Mn, 0.25 mM Fe, pH 6.5)

Residence time ca. 12 h

Fig. 16: Continuous gluconic acid fermentation with *A. pullulans* (3 g/l NH$_4$Cl, 1 mM Fe, 5 mM Mn, 450 g/l glucose)

Residence time ca. 20 h

Fig. 17: Continuous gluconic acid fermentation with *A. pullulans*; Influence of temperature (residence time ca. 12-13 h)

Fig. 18: Gluconic acid fermentation with *Aureobasidium pullulans* (fed batch) (3 g/l $NH_4Cl$, 5 mM Mn, 1 mM Fe, So 750 g/l, pH 6.5)

PROCESS FOR THE PRODUCTION OF GLUCONIC ACID WITH A STRAIN OF AUREOBASIDIUM PULLULANS (DE BARY) ARNAUD

This is a continuation of application Ser. No. 08/069,202 filed on May 28, 1993, now abandoned.

BACKGROUND OF THE INVENTION

1. Field of the Invention

This invention relates to a process for the production of gluconic acid by fermentation in aqueuos fluid containing sugar. In addition, this invention also relates to the microorganisms suitable for producing gluconic acid by fermentation in aqueuos fluid containing sugar.

2. Background Information

Gluconic acid is a multifunction carbonic acid. Due to the physiological and chemical characteristics of gluconic acid, gluconic acid is used extensively as the acid itself or as a salt of the acid, in particular a sodium salt. Gluconic acid can be used both for cleaning purposes and can also be used in the pharmaceutical, food and beverage industries. In the pharmaceutical, food and beverage industries, gluconic acid is used, in particular, as a preservative. Gluconic acid can also be used in the construction, wherein gluconic acid can be used as a cement additive to increase the cements resistance to fracture and to frost and water.

Gluconic acid can be obtained by chemical synthesis, on account of its superior selectivity, however, microbial production is preferred. A series of microorganisms such as Aspergillus and Penicilliun, many bacteria such as Gluconobacter-spec., Pseudomonas, Phytomonas, Achromobacter, Kiebsiella, *Zymomonas mobilis* and *Acetobacter methanolicus* have already been indicated as being usable for such microbial production of gluconic acid. *Aspergillus niger* and *Gluconobacter oxidans* are the most applied microorganisms. It has also been known for some time that yeast-like fungus cultures, such as *Aureobasidium pullulans* which are characterized by polymerizations, can form small amounts of gluconic acid (V. V. Pervozvanskii Microbiology (U.S.S.R.), 8, 149 [1939]).

However, the gluconic acid formation activities thereof have been known to be so small that production on an industrial scale was out of the question.

As described comprehensively in Ullmann's "Enzyklopaedie der Technischen Chemie" [Ullmann's Encyclopaedia of Industrial Chemistry], 1989, Volume A12, page 449 ff., for microbial production of gluconic acid, essentially only *Aspergillus niger* (predominantly), or *Gluconobacter suboxidans* have been applied for the industrial production of gluconic acid, though it is known that *Aspergillus niger* is difficult to handle as it can cause clogging and it is unsuitable for continuous production, as cell growth and gluconic acid formation would not be possible simultaneously. On the other hand, gluconobacter has been found to produce a relatively large quantity of keto-acids during production, which keto-acids can complicate processing and isolation of the gluconic acid.

OBJECTION OF THE INVENTION

Because of the above-discussed inadequacies and problems associated with microbial production of gluconic acid, it is the object of the present invention to find an alternative microorganism capable of producing gluconic acid, and to provide a corresponding and more efficient process for carrying out the gluconic acid production using the microorganism.

SUMMARY OF THE INVENTION

Surprisingly, it has now been discovered that industrial gluconic acid production using a phyla, or strain of *Aureobasidium pullulans* (de bary) Arnaud can be altogether advantageous for producing the gluconic acid. The indicated strain of *Aureobasidium pullulans* (de bary) Arnaud is a yeast which has been found to be astonishingly osmo-tolerant, and thus this yeast can be processed in economically profitable concentration ranges, whereby production can essentially be conducted continuously, if desired. It has surprisingly been determined that, under the appropriate conditions, the yeast proves to be a gluconic acid producer which can be used for a long period of time in continuous culture.

It has also been discovered that production strains can be isolated from this ubiquitous yeast, which strains achieve a high selectivity and product concentration with high glucose conversion. Particular requirements for economically profitable production are optimum iron ion and manganese ion concentrations, which have been found to be surprisingly high.

The process based on these discoveries for the production of gluconic acid according to the present invention can therefore essentially be characterized by the fact that the following production conditions be maintained:

use of a strain of *Aureobasidium pullulans* (de bary) Arnaud to form gluconic acid in continuous culture from glucose greater than or equal to about 200 g/l at greater than or equal to about 90% conversion and greater than or equal to about 90% molar selectivity;

performance of the process in a medium containing optimum concentrations of Fe and Mn, with an N-dependent iron and/or manganese ion concentration in the feed, which concentrations of Fe and Mn, with an N-concentration corresponding to about 3 g/l $NH_4Cl$ are greater than or equal to about 0.5 mM for Fe and greater than or equal to about 0.5 mM for Mn;

performance of the process at pH values from about 4.5 to about 8; and performance of the process at temperatures of about 24° C. to about 32° C.

Particularly active strains of *Aureobasidium pullulans* (de bary) Arnaud can be isolated in particular from wildflowers.

It can be appropriate if, during the principal blooming season, which extends from about March to about June, in particular, the flowers and stems of preferably Central European wildflowers are placed in shaking tubes in a preferably comminuted form, and if an acid solution containing glucose is used as a nutrient. The procedure can preferably be conducted a pH values around 2.5, and citric acid can be used for acidification. The culture liquid should preferably contain relatively high glucose concentrations, in particular around 100 g/l, and also a wetting agent, such as Tween 40, can be added. Since the strains which form gluconic acid are strictly aerobic, a good oxygen supply must be provided, and this can, in particular, be achieved by vigorous shaking.

In this matter, in particular the strains with the registration numbers DSM 7085 to 7088 in the Deutsche Sammlung von Mikroorganismen und Zellkulturen gmbh, Braunschweig [The German Collection of Microorganisms] can be isolated. These particular strains have been found to be capable, in the shaking flask, of producing gluconic acid concentrations of greater than about 100 g/l within about 2 days.

The above cited strains of *Aureobasidium pullulans*, that is, the strains DSM 7085, DSM 7086, DSM 7087, and DSM 7088 (DSM 7085 to DSM 7088), were all deposited on May 29, 1992, under the terms of the Budapest Treaty, at the DSM-Deutsche Sammlung von Mikroorganismen und Zellkulturen GmbH, Mascheroder Weg 1 B, D-3300 Braunschweig, Germany, and have been assigned the DSM reference numbers as so indicated.

The sugar solution which can be used for the conversion should preferably contain glucose, or contain a constituent which is able to form glucose. Starch hydrolysates, molasses, maltose, etc. are some examples of constituents which can be used.

Glucose concentrations of around 150 g/l are appropriate for gluconic acid production, whereby ranges of about 20 to about 400 g/l glucose seems useful in the batch process. In the fed-batch process during the growth phase, concentrations of around 150 g/l glucose can also be present, and values of about 100 g/l to about 200 g/l are preferred. Such high glucose concentrations can be achieved, in particular, by adding a highly-concentrated solution, which can contain up to approximately 800 g/l glucose. The continuous fermentation process is preferably conducted with feed concentrations of approximately 300 g/l to about 600 g/l, whereby conversions of greater than or equal to about 90% and selectivities of greater than or equal to about 90 Mol % can be achieved. Favorous molar selectivities obtained amounted to $\geq$95 Mol %.

The pH in the fermentation medium is preferably kept between about 6.0 to about 7. The appropriate temperature is preferably in the range of about 29° C. to about 31° C.

The appropriate concentrations of iron, manganese and magnesium ions in the feed are preferably a function of the nitrogen content of the medium. In the medium with nitrogen concentrations corresponding to about 3 g/l $NH_4Cl$, the concentration of iron, manganese and magnesium ions can be selected in particular in the range of about 0.5 mM to about 3 mM (for iron), about 2.5 mM to about 5 mM (for manganese ions) and about 1 mM to about 2 mM (for magnesium ions).

The gluconic acid formation according to the present invention can be operated as a batch or fed-batch process, but a continuous fermentation appears to be particularly appropriate, in particular with residence times of between about 10 to about 40 hours.

A good supply of oxygen has also been found to be important for the production of gluconic acid according to the present invention. For continuous production, the dissolved oxygen is essentially a function of the residence time, e.g. about 80% to about 150% saturation for a residence time of about 13 hours. Higher oxygen saturations are appropriate for longer residence times.

Although a fermentation in a fluidized bed reactor with biomass on a support or carrier may be more convenient from a process point of view, a fermentation with non-supported microorganisms and biomass retention is preferred. In this case, higher dissolved oxygen concentrations of greater than or equal to about 200% saturation are desirable.

For continuous production, a cascade series of at least two fermenters is favorable. In the first stage, the oxygen saturation is preferably between about 120% to about 170% and the residence time is preferably on the order of about 10 hours to about 25 hours, and in particular between about 12 hours to about 18 hours. In the second stage, or fermenter, the oxygen saturation is preferably greater than about 360% and the total residence time is preferably greater than or equal to about 15 h, in particular between about 18 hours to about 30 hours.

In addition to the above-mentioned metal ion concentrations in the medium, the phosphate concentration has also been found to be important, It has been found that greater than or equal to about 0.7 g/l $KH_2PO_4$ (with N concentrations corresponding to 3 g/l $NH_4Cl$), added to the feed, can be appropriate. For N concentrations corresponding to 1.5 g/l $NH_4Cl$, the $KH_2PO_4$ concentration in the feed should advantageously be about 0.34 g/l to about 2.4 g/l, and in particular about 0.7 g/l to about 2.1 g/l.

The nutrient medium should also contain ions of zinc, cobalt, copper, calcium, iodine, chlorine, boric acid, sulfate, and molybdate, as well as vitamins such as thiamine, biotin, pantothenate and nicotinic acids, and pyridoxine.

By connection at least two fermenters in series, in which the same reaction conditions prevail, particularly high conversion rates and gluconic acid yields can be obtained. In this manner, a high space-time yield can be achieved in the first fermenter, and a maximum conversion rate and a maximum yield can be achieved in the subsequent fermenter or fermenters, whereby high oxygen saturation values are advantageous in the second and possibly any subsequent stages.

Additional features of the process and microorganisms of the present invention are described below on the basis of examples, with reference to the accompanying drawings.

One aspect of the invention resides broadly in a process for the production of gluconic acid by fermentation in aqueous liquid containing sugar. The process comprising the application of a strain of *Aureobasidium pullulans* (de bary) Arnaud producing gluconic acid, and being able of forming the gluconic acid in a commercial scale.

Another aspect of the invention resides broadly in an *Auerobasidium pullulans* (de bary) Arnaud strain isolated from wildflowers by cultivation under acid conditions with increased glucose concentration and good oxygen supply.

One addition aspect of the invention resides broadly in an *Aureobasidium pullulans* (de bary) Arnaud strain having one of the following registration numbers: DSM 7085; DSM 7086; DSM 7087; and DSM 7088.

BRIEF DESCRIPTION OF THE DRAWINGS

The enclosed drawings are included to illustrate the dependence of gluconic acid production on individual parameters. In particular, continuous gluconic acid fermentation is examined, using Aureobasidium strain DSM 7085, which was found to have the highest activity. In the drawings and the accompanying description, the strain DSM 7085 may also be referred to as "isolate No. 70". In the drawings.

DESCRIPTION OF THE PREFERRED EMBODIMENTS

Figure 1:
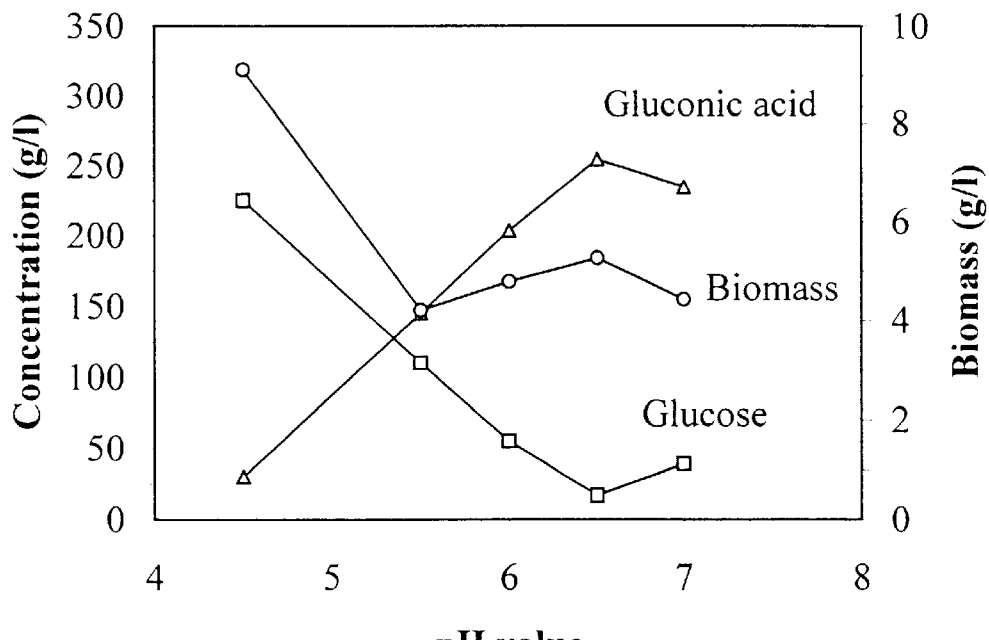
FIGS. 1 and 2 show the pH dependence.

The subsequent tests were performed at about 30° C. The organisms, however, are also capable of growth at lower temperatures, i.e. below about 30° C.

EXAMPLE 1

Isolation of *Aureobasidium Pullulans* (de bary) Arnaud

For the isolation of the phyla, wildflowers from Jülich, Düsseldorf, Heidelberg and Holland were comminuted and introduced into shaking flasks which contained a medium having the following concentration;

| | |
|---|---|
| Glucose | 100 g/l |
| Yeast extract | 3 g/l |
| Citric acid | 10 g/l |
| Tween 40 | 2 drops/liter |

The medium was autoclaved 15 minutes at 121° C.

The pH was adjusted to about 2.5–2.6 using citric acid. The charges in the shaking flasks were incubated at about 30° C. on a shaking machine (at about 200 rpm) for 1 or 2 days. As soon as a clouding of the isolating medium was detected, samples were spread on agar plates using an inoculating eyelet and dilute samples were spread using a Trikalsky spatula. The agar plates contained screening media having one of the following compositions:
Screening Medium:

| | |
|---|---|
| Medium I | |
| Glucose | 100 g/l |
| Yeast extract | 5 g/l |
| MgSO$_4$o 7aq | 0.5 g/l |
| KH$_2$PO$_4$ | 1 g/l |
| CaCO$_3$ | 5 g/l or 10 g/l |
| Agar | 20 g/l |
| Thiamine-HCl | 0.1 g/l (sterile filtered) |
| Medium II | |
| Glucose | 100 g/l |
| YBN (yeast base nitrogen) | 6.7 g (sterile filtered) |
| CaCO$_3$ | 7 g/l |
| Agar | 20 g/l |

The inoculated plates were incubated at about 30° C. for about 2 to about 5 days. Acid-producing microorganisms can be easily detected, because the acid formed dissolves the CaCO$_3$ and forms a clear lysis circle. The acid-producing microorganisms were isolated in pure culture on the above-mentioned medium, and then on a culture medium (which was a yeast-malt-extract-agar for fungus and yeasts), and were incubated at about 30° C. for about 1 to 2 days. Then the isolates obtained were kept at about 4° C. and some were also frozen at about −20° C. and about −80° C. in a medium containing 30% glycerin. The most important isolates were lyophilized.

The strains isolated had a characteristic pink color. They are strongly aerobic, i.e. they are incapable of growth without oxygen.
Colony Characteristics:
  On malt extract medium:
  smooth like yeast, edge fringed by mycelium;
  initially weak pink, later dark brown in spots.
  Colony diameter approximately 40 millimeter after 7 days at 25° C.
Morphology:
  Hyphae colorless, frequently septate, initially thin-walled, later also dark-brown in spots and thick-walled.
  Undifferentiated, intercalary or terminal cells forming conidiospores. Blasto-conidiosporos are formed simultaneously in groups, ellipsoid, size very variable (in a range of from about 3–7× about 7–16 micrometers), generally with short hilus at the point of detachment. Partial formation of endoconidiospores (about 3×6 micrometers).

The isolated microorganisms can be grown on maltose as the single carbon source, in addition to glucose. This characteristic can be beneficial with the use of cheap starch-partial hydrolysates containing maltose. The microorganisms grow slowly on mannitol. They can easily be immobilized on porous sintered glass and are suitable for continuous gluconic acid production with immobilized cells.

EXAMPLE 2

Gluconic Acid Production

The microorganisms isolated as described above were tested in a shaking flask. CaCO$_3$ was added to the medium to neutralize the acid formed. The screening medium contained the following components:

| | |
|---|---|
| Glucose | 100 or 150 g/l |
| NH$_4$Cl | 0.3 g/l |
| MgSO$_4$o 7aq | 0.2 g/L |
| KH$_2$PO$_4$ | 0.3 g/l |
| Yeast extract | 0.05 g/l |
| Thiamine-HCl | 0.1 mg/l |
| CaCO$_3$ | 20 or 40 g/l |

For the production of acid, 500 milliliter shaking flasks, which contained 50 milliliter of the above-mentioned fermentation liquid, were inoculated from fresh cultures of the isolated strains using an eyelet, and the shaking flasks were incubated for about 48 hours at about 30° C. on a shaking machine operating at about 200 rpm.

The acid concentrations present in the tubes were measured quantitatively with an HPLC device (RP$_{18}$ column, 2% acetonitrile and 5 mM TBA as a mobile phase, with 1 milliliter/min flow rate) at room temperature. Detection was performed with a UV detector at 210 NM.

With *Aureobasidium pullulans* isolates, it was possible to achieve gluconic acid concentrations of between about 22 and about 140 g/l within 2 days, with the concentration being a function of the CaCO$_3$ concentration used, and in the presence of about 0.3 g/l NH$_4$CL as the nitrogen source. The best results were achieved with about 40 g/l CaCO$_3$ at an initial glucose concentration of 150 g/l. Selected isolates were registered under Nos. DSM 7085, DSM 7086, DSM 7087 and DSM 7088 at the Deutsche Samnlung von Mikroorganismen [German Collection of Microorganisms].

EXAMPLE 3

Influence of pH on Gluconic Acid Production with Aureobasidium Strains.

The isolated phyla produce gluconic acid in a pH range between about 3.5 and about 8. A pH between about 5.5 and about 7.5 is preferred, with the optimum pH being about 6.5.

After about 27.5 hours in a batch process in a small fermenter, the strain DSM 7086 produced 13.74 g/l of gluconic acid at a pH of 4, 22.63 g/l at a pH of 5, 42.51 g/l at a pH of 6, and 67.71 g/l at a pH of 7.

TABLE

Influence of pH on gluconic acid production with DSM 7086

| pH | Time (h) | Gluconate g/l |
|----|----------|---------------|
| 4  | 27.5     | 13.74         |
| 5  | 27.5     | 22.63         |
| 6  | 27.5     | 42.51         |
| 7  | 27.5     | 67.71         |

|                  | Inoculum  | Fermentation Medium |
|------------------|-----------|---------------------|
| Glucose          | 30 g/l    | 150 g/l             |
| $NH_4Cl$         | 0.3 g/l   | 0.3 g/l             |
| $KH_2PO_4$       | 0.3 g/l   | 0.3 g/l             |
| $MgSO_4.7Aq$     | 0.2 g/l   | 0.4 g/l             |
| Yeast extract    | 0.05 g/l  | 0.05 g/l            |
| Thiamine-HCl     | 0.1 mg/l  | 0.1 mg/l            |
| $CaCO_3$         | 5 g/l     | —                   |
| Temperature      | 30° C.    | 30° C.              |
| pH-value         | —         | 4–7                 |
| Oxygen supply    |           | 5 l/h pure oxygen   |

EXAMPLE 4

Influence of pH on Continuous Gluconic Acid Fermentation with DSM 7085.

The optimum pH for growth and production with DSM 7085 was investigated in continuous chemostat experiments (in the same small fermenter), under otherwise identical fermentation conditions. With a constant substrate feed, the residence time was 21.86 and 25.51 hours, as a function of the NaOH consumed. It required more than about five residence times to achieve steady state conditions.

|                    | Fermentation Medium                  |
|--------------------|--------------------------------------|
| Glucose            | 360 g/l                              |
| $NH_4Cl$           | 3 g/l (measured 761 mg/l nitrogen)   |
| $KH_2PO_4$         | 0.7 g/l                              |
| $MgSO_4.7aq$       | 0.35 g/l                             |
| $CuSO_4.5aq$       | 100 micrograms/l                     |
| $Na_2MoO_4$ 2aq    | 200 micrograms/l                     |
| $ZnSO_4.7aq$       | 0.01 g/l                             |
| $CoSO_4.7aq$       | 4 mg/l                               |
| $H_3BO_3$          | 0.04 g/l                             |
| $MnSO_4$ 4aq       | 5 mM                                 |
| $FeSO_4$ 7aq       | 100 micromolar                       |
| $CaCl_2$           | 0.1 g/l                              |
| NaCl               | 0.1 g/l                              |
| KJ                 | 0.1 mg/l                             |
| Citric acid        | 2.5 g/l                              |
| Thiamine-HCl       | 2 mg/l                               |
| Biotin             | 0.25 mg/l                            |
| Pyridoxin-HCl      | 0.625 mg/l                           |
| Ca-D-pantothenate  | 0.625 mg/l                           |
| Nicotinic acid     | 0.5 mg/l                             |
| Temperature        | 30° C.                               |
| pH correction      | 22.5% NaOH solution                  |

The $NH_4Cl$ and vitamin solutions were sterile filtered.

Figure 2:
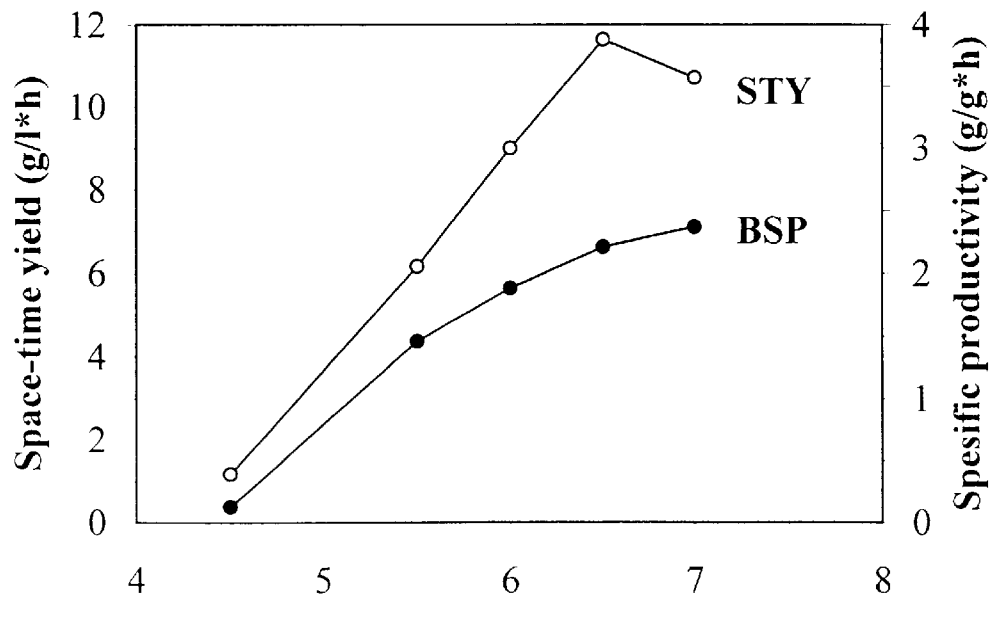

With the strain DSM 7085, it has been determined that gluconic acid can be continuously produced in a pH range between about 3.5 and about 8 (FIG. 1). As shown in FIG. 2, the highest space-time yield was achieved at a pH of about 6.5, and was 11.64 g/l*h with a residence time of about 21.86 hours. The biomass-specific productivity increased with increasing pH, and was 2.08 g/g*h at pH of 7. The selectivity (mol product/mol converted glucose), with the exception of the sample taken at pH of about 4.5, was above 90%, and it was almost 100% at pH between 5.5 to 6. The highest conversion rates (g converted glucose/g glucose input) and the maximum yield (mol product/mol glucose input) were achieved at a pH of abut 6.5 (FIGS. 1 and 2).

At lower pH values (for example, a pH of abut 4.5), the selectivity, space-time yield and biomass-specific productivity were very poor, but the highest biomass concentration was observed. The high viscosity of the fermentation solution is essentially due to the formation of polymers. Auerobasidium strains are known for the formation of pullulane. The polymer formation can be repressed at pH values above about 4.5.

EXAMPLE 5

Influence of Oxygen on Gluconic Acid Fermentation with Aureobasidium Strains.

The oxygen supply, as with *Aspergillus niger*, is of major importance for gluconic acid fermentation with the isolated Aureobasidium strains.

A direct oxygen-dependence was observed with shaking tubes and small fermenter experiments. An isolate from wildflowers originating from Holland produced about 54.17 g/l gluconic acid in shaking tubes without baffle plates and about 97.8 g/l gluconic acid in the shaking tubes with baffle plates. The following table indicates the influence of the oxygen.

TABLE

Influence of oxygen on glucose consumption

| Ventilation | Glucose consumption after 48 hours (g/l) |
|-------------|------------------------------------------|
| 1. Shaking tubes without baffle plates | 57 |
| 2. Shaking tubes with baffle plates    | 100 |
| 3. $N_2$ (small fermenter)             | 0.7 |
| 4. 0.3 vvm (oxygen from air)           | 9.8 |
| 5. 1.4 vvm                             | 22.5 |

For fermentations with additional isolates in the small fermenter (with magnetic agitator), an oxygen feed using air was not sufficient for optimum gluconic acid production. In the subsequent experiments, therefore, the process was performed with pure oxygen, to simulate the better oxygen supply in the agitator vessel, (stirred fermenter).

EXAMPLE 6

Influence of Oxygen on Continuous Gluconic Acid Fermentation with DSM 7085.

The influence of oxygen was investigated in further detail in an agitator vessel (Biostat E, Braun-Diessel) in the continuous process with the production phylum DSM 7085, with residence times between about 12 to about 13 hours. The air/oxygen ratio in the tests was varied. The composition of the fermentation medium, except for an iron concentration which was increased to 0.5 mM and a copper sulfate concentration of 1 mg/l, was essentially the same as the composition in Example 4.

The dissolved oxygen concentration can have an effect both on growth (FIG. 3) and on gluconic acid production (FIG. 5), and also on various factors such as conversion, space-time yield, biomass-specific productivity (FIG. 4), selectivity and yield.

Using DSM 7085, gluconic acid can essentially be produced when the concentration of dissolved oxygen is between about 40% and about 360% (100% corresponds to oxygen saturation with oxygen from the air). The biomass-specific productivity increases in linear fashion with increasing dissolved oxygen concentration, and was found to be about 3.2 g/g*h with a residence time of about 13.29 hours and dissolved oxygen concentration of about 360%.

Figure 3:
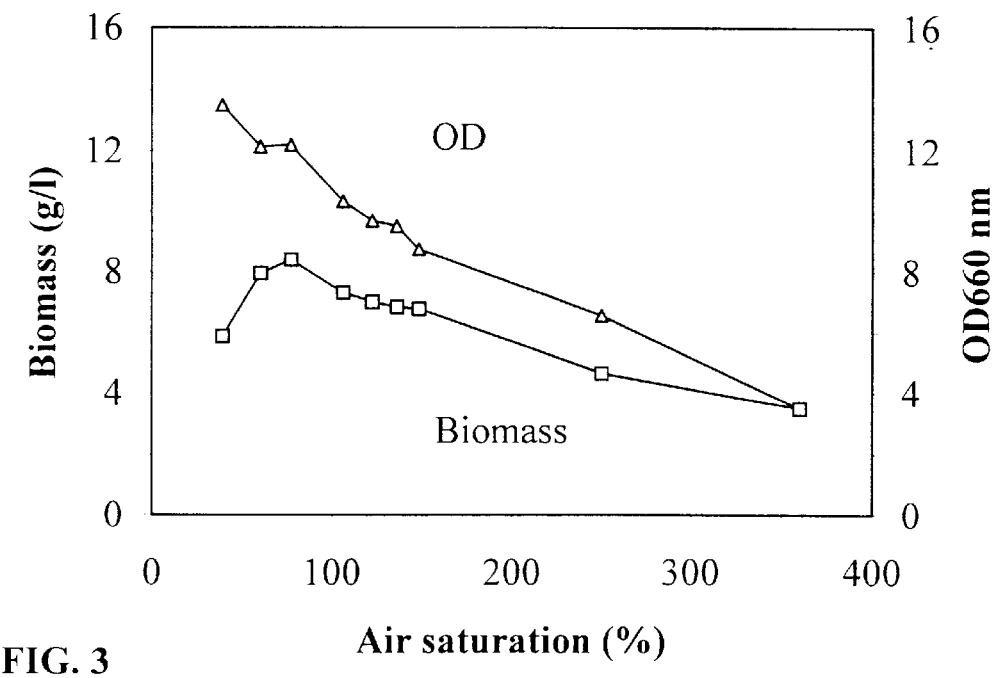
FIGS. 3 to 5 show the influence of the dissolved oxygen concentration.

Growth was found to increase when the dissolved oxygen concentration was in a range of between about 39% and about 77%, and was found to decrease again at higher dissolved oxygen concentrations. A correlation can also be observed in the $CO_2$ content of the exhaust. The optical density essentially does not correlate with the biomass concentration, and was found to decrease in linear fashion as the oxygen concentration in the fermenter was increased from about 39% to about 360%. This can essentially be explained by a process called pellet formation (lower optical density) at higher oxygen concentrations, and may have a protective function (FIG. 3).

Figure 4:
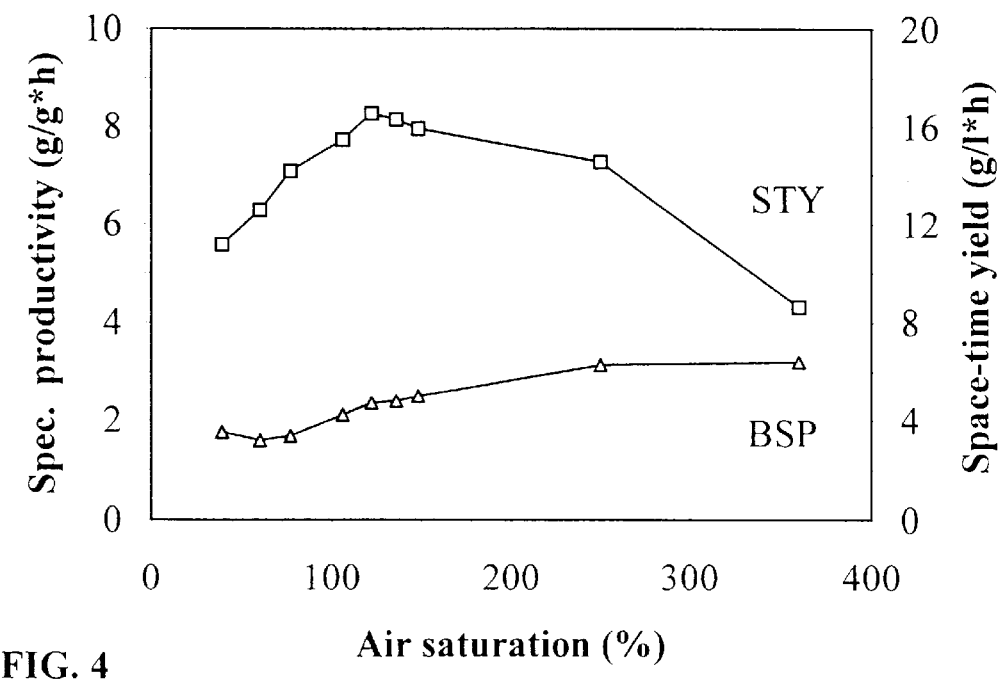
Figure 5:
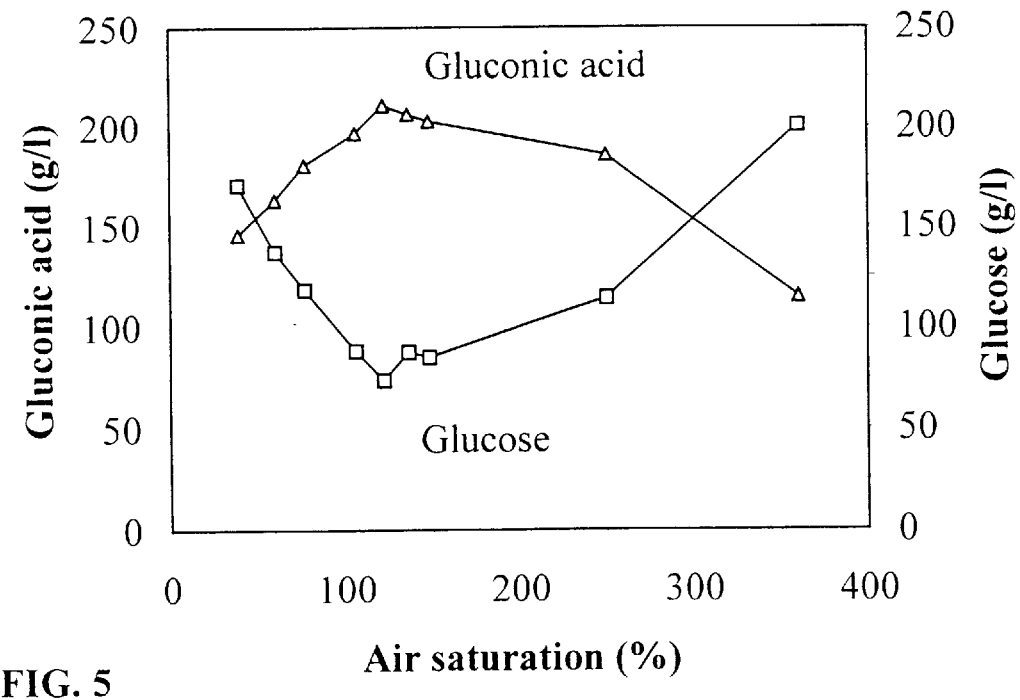

The space-time yield reaches its maximum of about 16.57 g/l*h at a dissolved oxygen concentration of about 122% and a residence time of about 12.71 hours (FIG. 4). The selectivity in the entire dissolved oxygen range was about 90%. During these short residence times, it was possible to continuously produce more than 200 g/l gluconic acid. The use of higher glucose concentrations and a biomass retention with microfiltration, at high dissolved oxygen concentrations, can make it possible to maximize the gluconic acid concentration with short residence times. One alternative is the cultivation of the microorganism in a small fermenter under oxygen concentrations which are optimum for growth, and a conlinuous feed with the production medium into a second production fermenter with a high dissolved oxygen concentrations. It has also been determined that nitrogen limitation can have a positive influence on the specific factors.

EXAMPLE 7

Continuous Gluconic Acid Fermentation with DSM 7085 with Different Residence Times (X/D diagram)

The fermentation medium was essentially the same as in Example 4:

| Fermentation medium | |
|---|---|
| Glucose | 110 g/l and 249–300 g/l |
| $NH_4Cl$ | 3 g/l |
| $KH_2PO_4$ | 0.7 g/l |
| $MgSO_4 \circ 7$ aq | 0.35 g/l |
| $CuSO_4 \circ 5$ aq | 100 microgram/l |
| $ZnSO_4 \circ 7$ aq | 0.01 g/l |
| $CoSO_4 \circ 7$ aq | 0.004 g/l |
| $H_3BO_3$ | 0.04 g/l |
| $MnSO_4 \circ 4$ aq | 0.5 mM |
| $FeSO_4 \circ 7$ aq | 0.5 mM |
| $CaCl_2$ | 0.1 g/l |
| NaCl | 0.1 g/l |
| KJ | 0.1 mg/l |
| $Na_2MoO_4 \circ 2$ aq | 200 microgram/l |
| Citric acid | 2.5 g/l |
| Temperature | 30° C. |
| pH-value | 6.5 |
| Work volume | 500 ml |
| Correction | 22.5% NaOH solution |

Figure 6:
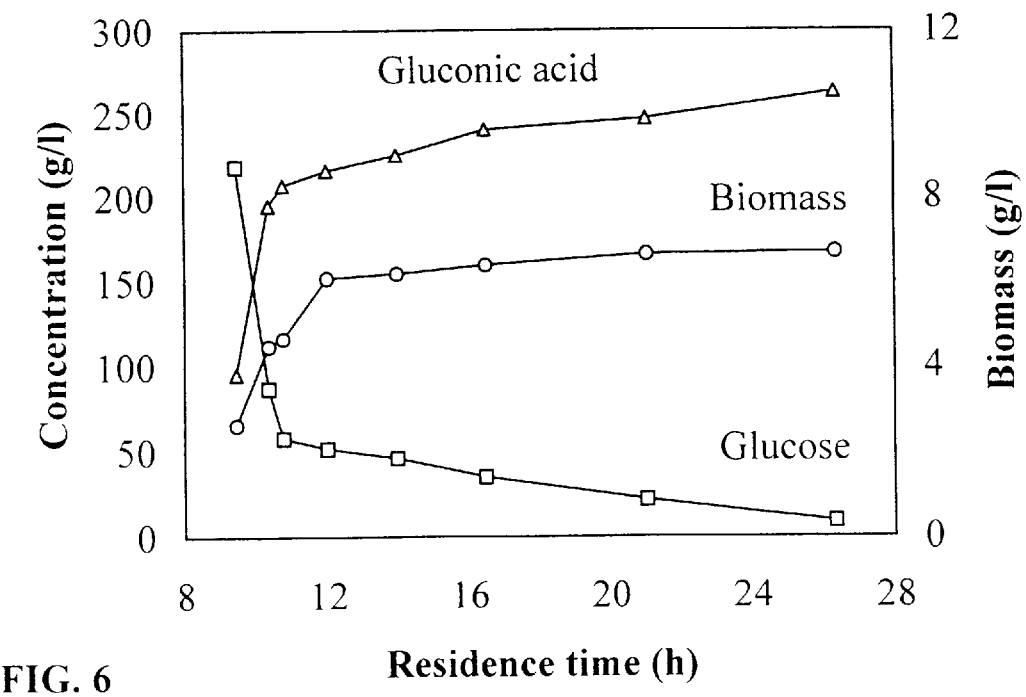
FIGS. 6 and 7 show the influence of the residence time.

For continuous gluconic acid formation with DSM 7085, when a glucose concentration of about 360 g/l is used with short residence times of approximately 10 to approximately 12 hours, more than about 200 g/l gluconic acid can be produced over a long period (FIG. 6). When higher glucose concentrations are used, the gluconic acid concentration can be maximized. The gluionic acid concentration essentially correlates with the curve of the biomass concentration, and decreases as the residence time decreases. The glucose concentration essentially behaves in the reverse fashion.

Figure 7:
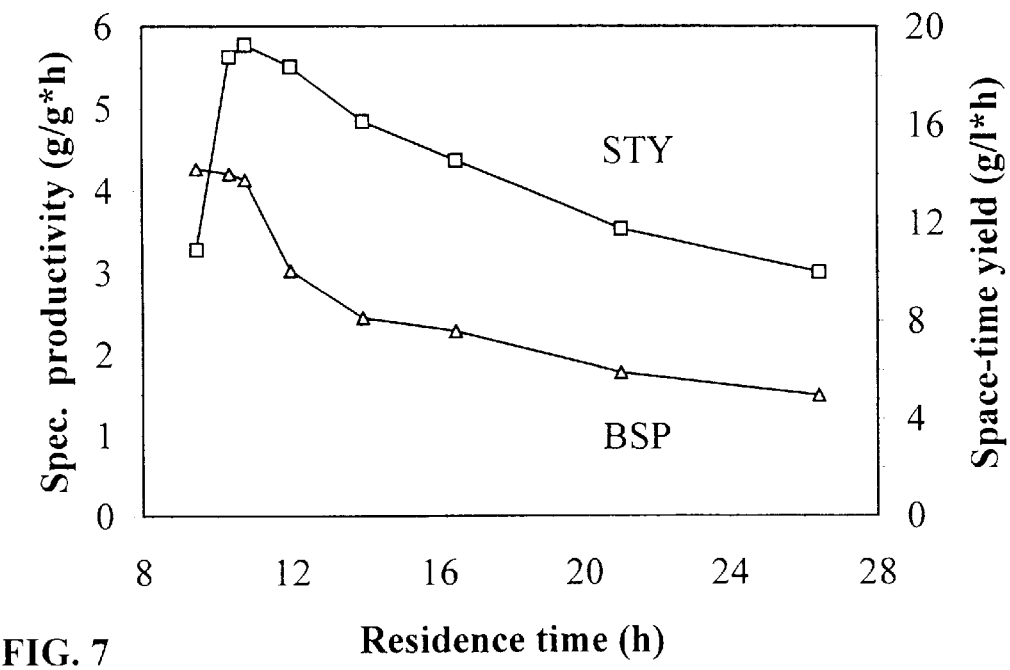

The space-time yield initially increases in a linear fashion when the residence time is decreased to about 10.77 hours, and then collapses at even shorter residence times. The biomass-specific productivity increases over the entire range as the residence time decreases (FIG. 7). The conversion and the yield (mol product/mol glucose input) essentially decrease, like the gluconic acid concentration, as the residence time decreases. The selectivity over the entire range is higher than about 90%. To maximize the gluconic acid concentration, it is more favorable to use residence times of more than about 20 hours and high glucose concentrations.

Alternately, a plot of an X/D diagram (not shown) using about 110 g/l glucose in the feed, the gluconic acid concentration was found to initially increase as the residence time decreases, and then decrease for very short residence times. With longer residence times, the gluconic acid formed is converted, and fumaric acid is formed as a byproduct.

EXAMPLE 8

Influence of Iron and Manganese on Batch Fermentation of Gluconic Acid

The growth of the Aureobasidium strains, and the gluconic acid production of the strains can be regulated with manganese and iron ions. With a defined minimum medium, when there is a deficiency of iron and manganese, and when there is a characteristic pellet-like growth, it is possible to achieve a selectivity of about 98% and a conversion rate of almost 100%.

But the influence of iron is not as great as the influence of manganese. At an $NH_4Cl$ concentration of about 0.3 g/l, strain DSM 7085 exhibits at similar gluconic acid production at iron concentrations between about 50 and about 500 micromolar.

| Composition of the Medium | | | | |
|---|---|---|---|---|
| | Inoculum | | Fermentation | |
| Glucose | 30 | g/l | 160 | g/l |
| $NH_4Cl$ | 3 | g/l | 0.3 | g/l |
| $KH_2PO_4$ | 0.7 | g/l | 0.3 | g/l |
| $MgSO_4 \circ 7$ aq | 0.35 | g/l | 0.2 | g/l |
| $MnSO_4 \circ 5$ aq | 50 | microgram/l | 0 and 10 | micromolar |
| $FeSO_4 \circ 7$ aq | 50 | microgram/l | 0 and 10 | micromolar |
| $ZnSO_4 \circ 6$ aq | 10 | mg/l | — | |
| $CoSO_4 \circ 7$ aq | 4 | mg/l | — | |
| $H_3BO_3$ | 40 | mg/l | — | |
| $CaCl_2$ | 0.1 | g/l | — | |
| $CuSO_4$ 5 aq | 2 | mg/l | — | |
| Thiamine | 2 | mg/l | — | |
| Biotin | 0.25 | mg/l | — | |
| $CaCO_3$ | 5 | g/l | — | |
| Temperature | 30° C. | | 30° C. | |
| pH-value | — | | 6.5 | |
| Work volume | — | | 550 | ml |

Medium for Iron Influences Same as Above

| | |
|---|---|
| MnSO$_4$ o 4 aq | 0.5 mM |
| FeSO$_4$ o 7 aq | 50, 100, 250 and 500 micromolar |

A manganese limitation (10 micromolar iron and 0 micromolar manganese in the fermentation solution), as with the iron limitation, results in a selectivity of about 98% with a conversion rate of almost 100%. After about 54 hours, about 147 g/l of gluconic acid was produced using the medium indicated above. Pellet-like growth was also characteristic here. Without manganese and without iron, only about 32 g/l of gluconic acid was formed after about 54 hours. With about 0 micromolar iron and about 10 micromolar manganese, about 118.86 g/l of gluconic acid was formed, and with 10 micromolar iron and about 0 micromolar manganese, 147.07 g/l of gluconic acid was formed.

When the manganese concentration is increased, growth and production are accelerated. With 0.25 mM manganese and without iron, 29.08 g/l gluconic acid was formed after about 24 hours. With 0.5 mM manganese, 44.27 g/l was formed, and with 2 mM manganese, 35.67 g/l was formed. However, with 10 micromolar manganese, only 11 g/l was formed after 24 hours. The selectivity was greater than about 90%.

| | Inoculum same as above | | Fermentation same as above | |
|---|---|---|---|---|
| Glucose | 30 | g/l | 165 | g/l |
| MnSO$_4$ o 5 aq | 50 | micromolar | 0.25–2 | mM |
| FeSO$_4$ o 7 aq | 50 | micromolar | — | |

EXAMPLE 9

Influence of Manganese on Continuous Gluconic Acid Fermentation with DSM 7085

The influence of manganese was investigated in greater detail in continuous fermentations in the small fermenter. During these experiments, a medium like the one indicated in Example 4 was used, and only the manganese concentration was varied after each steady state. Manganese concentrations between about 0.25 mM and about 7.5 mM were used. It took at least about five residence times to reach the respective steady state.

| | | |
|---|---|---|
| Glucose | 360 | g/l |
| NH$_4$Cl | 3 | g/l |
| KH$_2$PO$_4$ | 0.7 | g/l |
| MgSO$_4$ o 7 aq | 0.35 | g/l |
| ZnSO$_4$ o 6 aq | 0.01 | g/l |
| CuSO$_4$ o 5 aq | 1 | mg/l |
| CoSO$_4$ o 7 aq | 4 | mg/l |
| H$_3$BO$_3$ | 0.04 | g/l |
| CaCl$_2$ | 0.1 | g/l |
| NaCl | 0.1 | g/l |
| KJ | 0.1 | mg/l |
| FeSO$_4$ o 7 aq | 0.1 | mM |
| MnSO$_4$ o 5 aq | 0.25–7.5 | mM |
| Temperature | 30° C. | |
| pH-value | 6.5 | |
| Work volume | 500 | ml |
| SKE | 1300 | |
| Residence time | ca. 18h; >20 h | |
| (Vitamins added as in example 4) | | |

Figure 8:
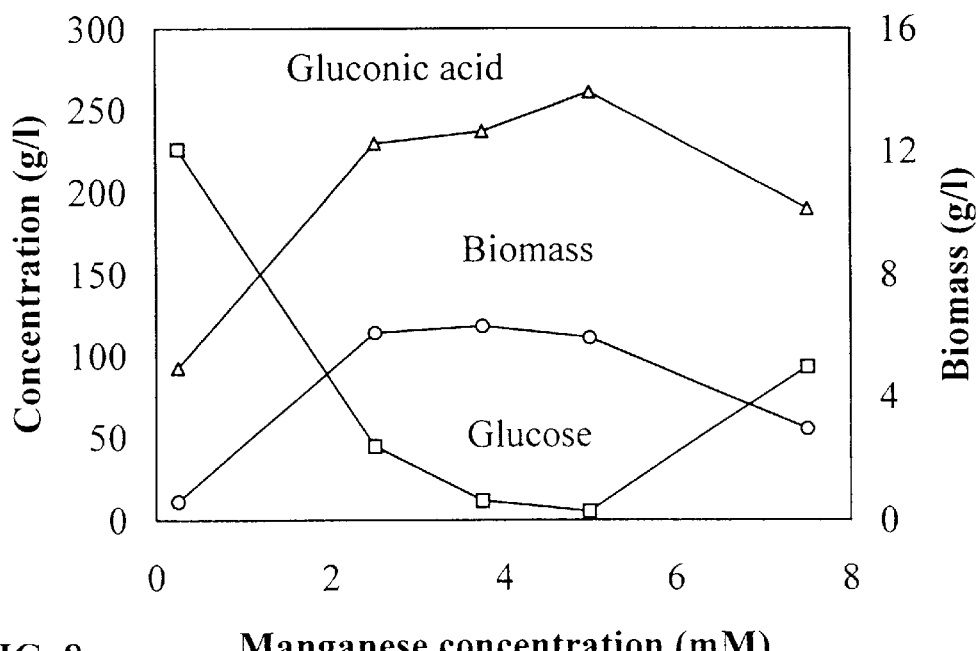
FIGS. 8 and 9 show the influence of the manganese concentration.
Figure 9:
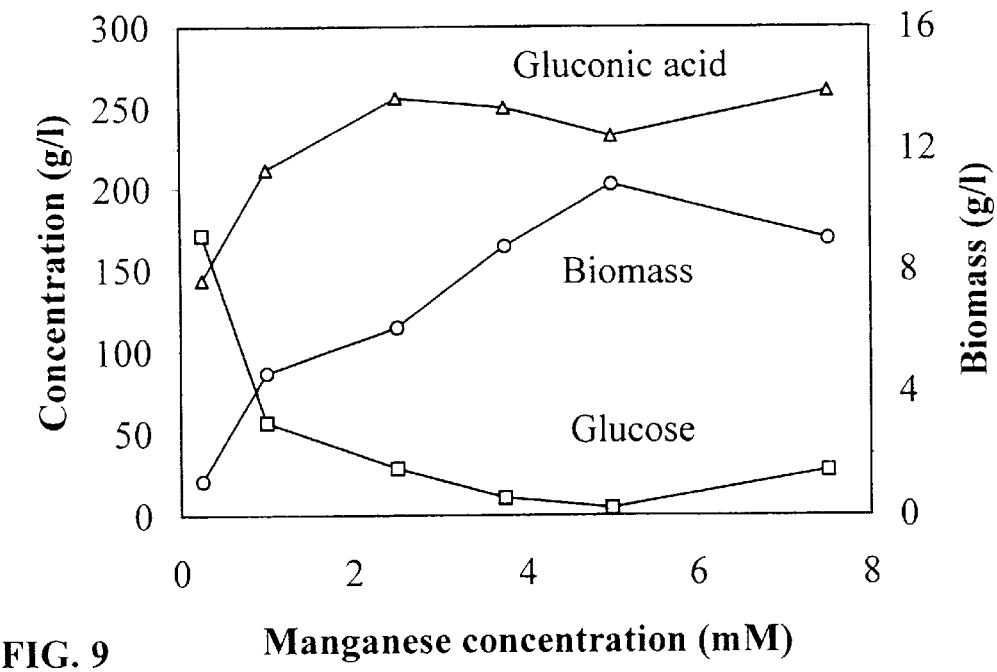

For continuous gluconic acid fermentation with DSM 7085, gluconic acid can be produced at manganese concentrations between about 0 mM and more than about 7.5 mM manganese. The optimum lies in the range of from about 2.75 mM to about 5 mM. With an increase of the manganese concentration from about 0.25 mM to about 5 mM manganese, the biomass increases and then decreases with a further increase. For residence times of more than about 20 hours, the glucose is essentially completely consumed in the presence of about 5 mM manganese, and some of the gluconic acid formed is converted (FIG. 9). At shorter residence times (ca. 18 h), it was shown that the highest gluconic acid concentration of about 260 g/l can be produced continuously with about 5 mM manganese (See FIG. 8). Above and below this manganese concentration, the gluconic acid concentration was found to decrease, and is only about 92.73 g/l (FIG. 8) at 0.25 mM Mn.

EXAMPLE 10

Influence of Iron on Continuous Gluconic Acid Fermentation with DSM 7085

| Fermentation medium (as in example 9) | | |
|---|---|---|
| NH$_4$Cl | 3 | g/l |
| MnSO$_4$ o 4 aq | 5 | mM |
| FeSO$_4$ o 7 aq | 0.1 to 2 | mM |

For continuous gluconic acid production, the differences over a broad spectrum of iron concentrations (from about 0.1 mM to about 2 mM), like those for the batch gluconic acid production, were not so great. Gluconic acid can be produced continuously in the presence of between about 0 to more than about 2 mM iron, and the preferred concentrations are between about 0.1 and about 1 mM iron.

The influence of iron was investigated in chemostat experiments with residence times of approximately 13 to approximately 18 hours. The medium used was indicated in Example 10. No measurable effects were observed (FIG. 11) at a residence time of approximately 18 hours and with almost complete conversion, but at shorter residence time and incomplete conversion (FIG. 11) some effects were observed.

Over a concentration range between about 0.1 to about 2 mM iron, there were no great differences observed in growth and gluconic acid production, compared to the influence of the manganese.

Figure 11:
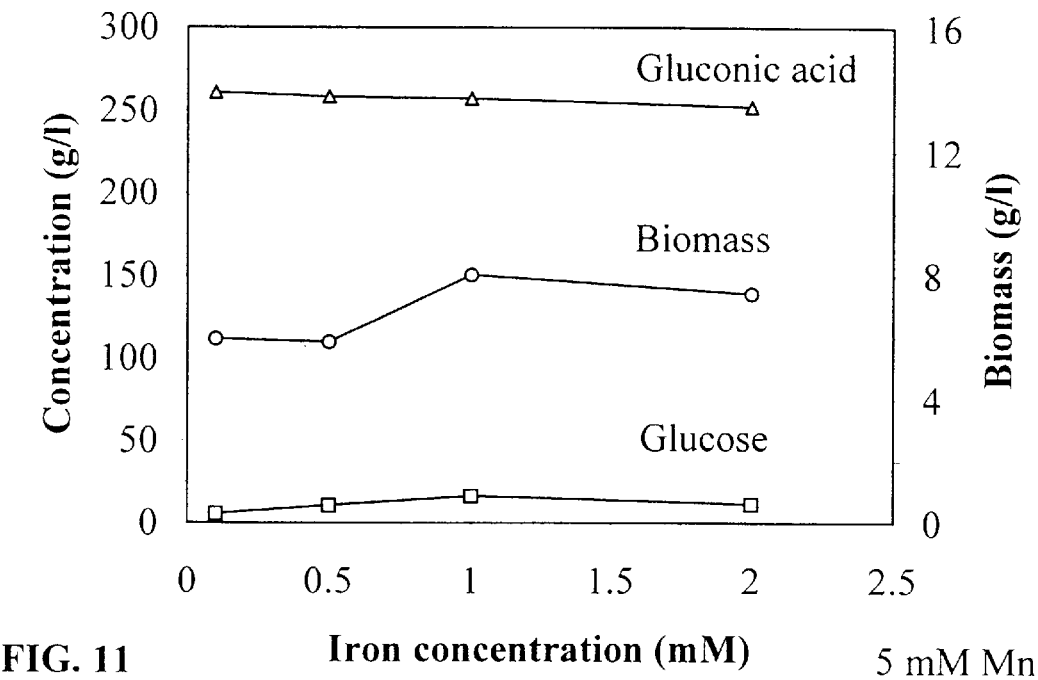

FIG. 11 shows the influence of iron on continuous gluccinic acid fermentation with a residence time of approximately 18 hours. With about 0.1 mM iron, about 5.96 g/l biomass could be formed, while about 7.4 g/l biomass could be formed with about 2 mM Fe. The nitrogen in the fermenter was measured over the entire range. The residual nitrogen concentration in the fermenter at about 0.1 mM Fe was about 197 mg/l, and at about 2 mM Fe the residual nitrogen was about 201 mg/l.

Figure 10:
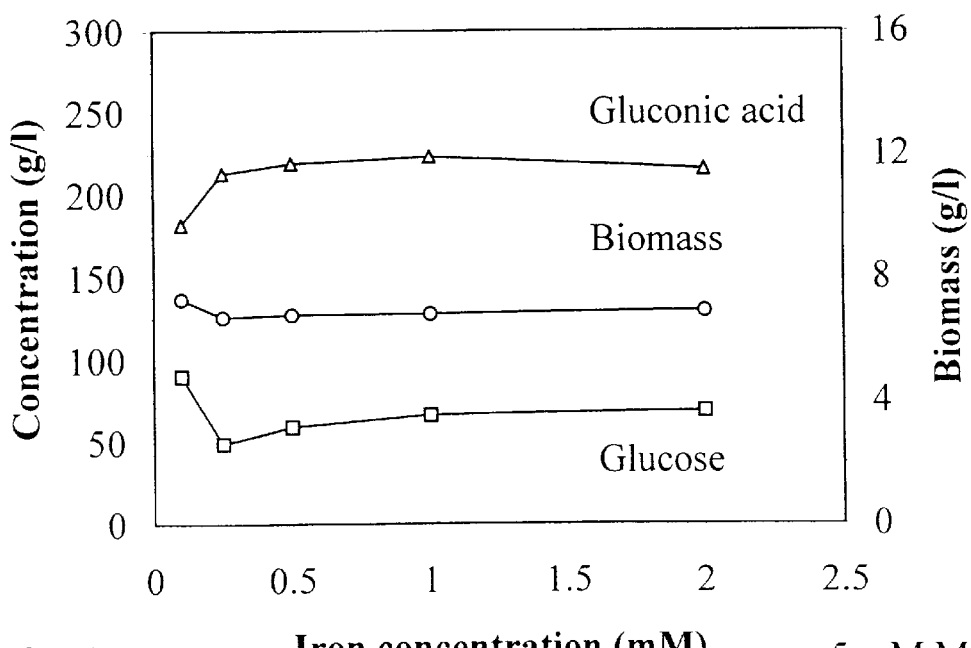
FIGS. 10 to 13 show the influence of the iron concentration.

Alternatively, with residence times of approximately 13 hours, 7.3 g/l biomass could be formed with an iron concentration of 0.1 mM, while 6.96 g/l biomass could be formed with 2 mM (FIG. 10).

The maximum gluconic acid concentration was 223.25 g/l, and was reached at 1 mM iron. 181.95 g/l of gluconic acid was formed at 0.1 mM Fe, and 215.66 g/l gluconic acid was formed at 2 mM. The maximum space-time yield and the maximum specific productivity were also achieved at 1 mM Fe, and were 16.81 g/(l*h) and 2.46 g/(g*h), respectively, at a residence time of 13.28 h. A space-time yield of 14.47 g/(l*h) and a specific productivity of 1.82 g/(g*h) were reached (FIG. 12) at 0.1 mnM iron and a residence time of 13.71 hours.

Figure 13:
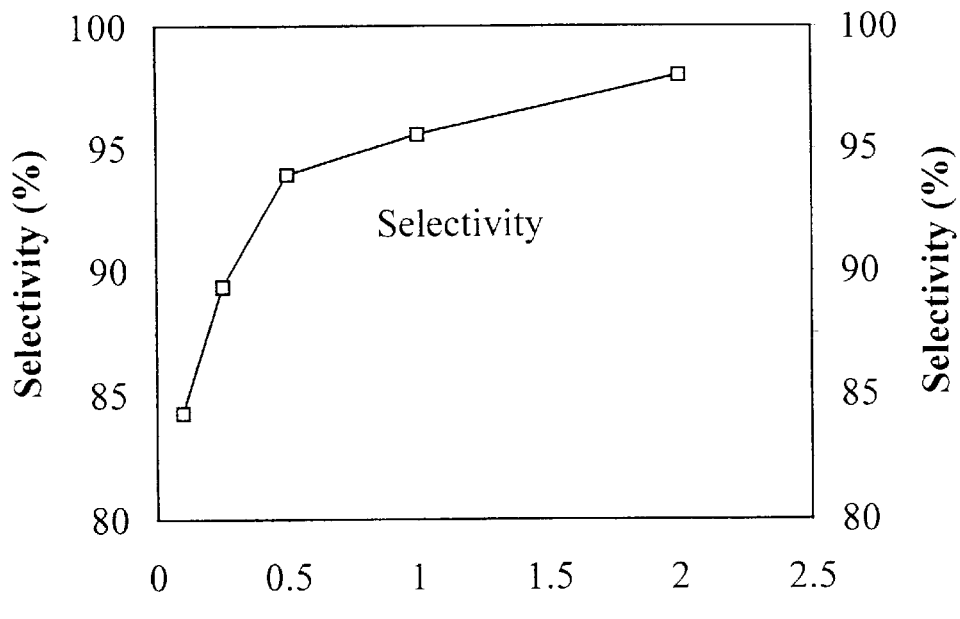

Surprisingly, significant differences in product selectivity (mol product/mol converted glucose) were observed as a function of the iron concentration used, with this short residence time (incomplete conversion). With an increasing iron concentration from 0.1 mM to 2 mM, the product selectivity increased continuously. At 0.1 mM the selectivity was 84.26%, and at 2 mM iron it was about 98%. With iron concentrations above about 0.5 mM, selectivity was more than 90% (FIG. 13).

The optimum residence time for the glucose concentration used is of major important for optimum production, and must be taken into consideration, since with very long residence times, the gluconic acid formed is partly converted.

More than 250 g/l gluconic acid was formed with all the iron concentrations tested at a residence time of approximately 18 hours. The highest gluconic acid concentration of 260.94 g/l was measured at 0.1 mM iron. 252.35 g/l gluconic acid were formed with 2 mM iron (FIG. 11). Although not plotted, the selectivity at approximately 18 hour residence times was found to decrease with increasing iron concentration, on account of the continued consumption of gluconic acid.

Figure 12:
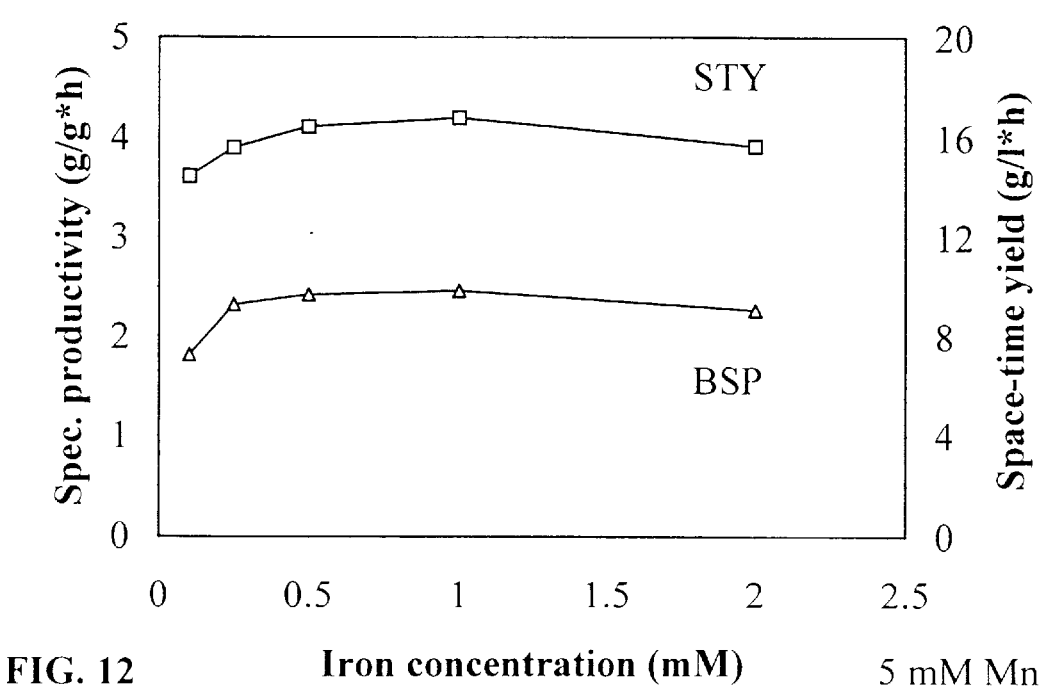

FIG. 12 shows the influence of iron on the specific productivity (BSP) and space-time yield (RZA) with a residence time of approximately 13 hours.

FIG. 13 shows the influence of iron on the product selectivity with a residence time of approximately 13 hours.

EXAMPLE 11

Influence of Nitrogen

Nitrogen limitation is also of major importance. The gluconic acid production in the batch process with the isolated strains is a three-phase process, and proceeds similar to a typical growth curve with a lag phase, followed by an accumulating log phase and a stationary production phase. For all the isolates tested, the maximum gluconic acid production essentially begins immediately after the consumption of the nitrogen.

With phosphorous limitation at 0.1 g/l $KH_2PO_4$, the influence of nitrogen was investigated in small fermenters at 30° C and a pH of 6.5. During these experiments 0.5 g/l, 1 g/l, 2 g/l and 4 g/l $NH_4Cl$ were used in four simultaneous fermentations, under otherwise identical conditions. Interestingly, even in spite of the left-over nitrogen, gluconic acid continued to be produced at the higher N concentrations. Gluconic acid production with the isolated microorganisms is apparently coupled to growth. The best specific productivities were measured at the lowest N concentration (0.5 g/l $NH_4Cl$). Surprisingly, better growth and better productivity were observed at the highest N concentration (4 g/l $NH_4Cl$) than at the intermediate concentrations (1 g/l and 2 g/l).

EXAMPLE 12

It was possible to produce more than about 400 g/l gluconic acid within two days in the fed-batch process using DSM 7085. The selectivity was greater than 90%, as with continuous fermentation. Following the growth phase, a 75% glucose solution was periodically added to the fermenter.

Medium Composition

| | Inoculum 10% | Fermentation Solution | Glucose Solution Feed |
|---|---|---|---|
| Glucose | 50 g/l | 150–300 g/l | 750 g/l |
| $NH_4Cl$ | 3 g/l | 3 g/l | — |
| $KH_2PO_4$ | 0.7 g/l | 0.7 g/l | 0.3 g/l |
| $MgSO_4*7aq$ | 0.5 g/l | 0.5 g/l | 0.2 g/l |
| $CuSO_4*5aq$ | 2 mg/l | 2 mg/l | — |
| $Na_2MoO_4*2aq$ | 200 micrograms/l | 200 micrograms/l | — |
| $ZnSO_4*7aq$ | 0.01 g/l | 0.01 g/l | — |
| $CoSO_4*7aq$ | 4 mg/l | 4 mg/l | — |
| $B_3BO_3$ | 40 mg/l | 40 mg/l | — |
| $CaCl_2$ | 0.1 g/l | 0.1 g/l | — |
| NaCl | 0.1 g/l | 0.1 g/l | — |
| KJ | 0.1 mg/l | 0.1 mg/l | — |
| Citric acid | 0.25 g/l | 0.25 g/l | — |
| Thiamine-HCl | 2 mg/l | 2 mg/l | 2 mg/L |
| Biotin | 0.25 mg/l | 0.25 mg/l | 0.25 mg/l |
| $CaCO_3$ | 5 g/l | — | — |
| pH-value | — | 6.5 | 6.5 |
| Temperature | 30° C. | 30° C. | 30° C. |
| $MnSO_4*4aq$ | 2.5–5 mM | 2.5–5 mM | |
| $FeSO_4*7aq$ | 0.1–0.5 mM | 0.1–0.5 mM | |

The strain DSM 7085 was grown even at a glucose concentration of about 360 g/l. The log phase began only after an extended lag phase. Therefore it is possible to use high glucose concentrations.

It is more logical, however, to start the process with glucose concentrations of approximately 150 g/l, and to add a highly-concentrated glucose solution or solid glucose to the fermenter.

EXAMPLE 13

Influence of Phosphorous on Continuous Gluconic Acid Fermentation with *Auerobasidium Pullulans* DSM 7085

In investigating the influence of phosphorous, a medium like that described in Example 10 was used, but with about half the amount of nitrogen, vitamins and trace elements, and with 0.25 mM iron. The tests were performed with residence times of approximately 12.5 and about 17 hours. The effect of the phosphorous was greater at the shorter residence time.

Figure 14:
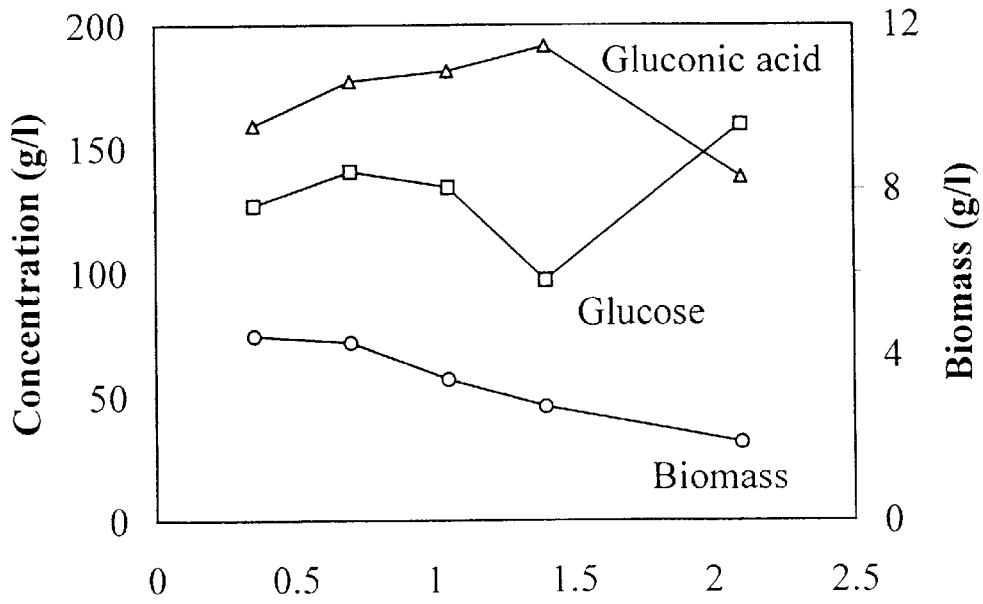
FIGS. 14 and 15 show the influence of the phosphate concentration.

FIG. 14 shows the influence of phosphorous on gluconic acid fermentation with a residence time of approximately 13 hours. The biomass concentration decreases continuously with increasing $KH_2PO_4$ concentration. With 0.35 g/l $KH_2PO_4$ (which corresponds to the initial concentration), 4.47 g/l of biomass was formed, and with 2.1 g/l $KH_2PO_4$, 1.91 g/l of biomass was formed. With a $KH_2PO_4$ concentration increasing from 0.35 g/l to 1.4 g/l, the gluconic acid concentration increased continuously. With 1.4 g/l $KH_2PO_4$, the highest product concentration of 191.35 g/l gluconic acid was achieved, which then decreased at higher $KH_2PO_4$ concentrations. By comparison, 158.99 g/l of gluconic acid was continuously formed at 0.35 g/l $KH_2PO_4$, and 138.36 g/l of gluconic acid was continuously formed at 2.1 g/l, (FIG. 14).

Figure 15:
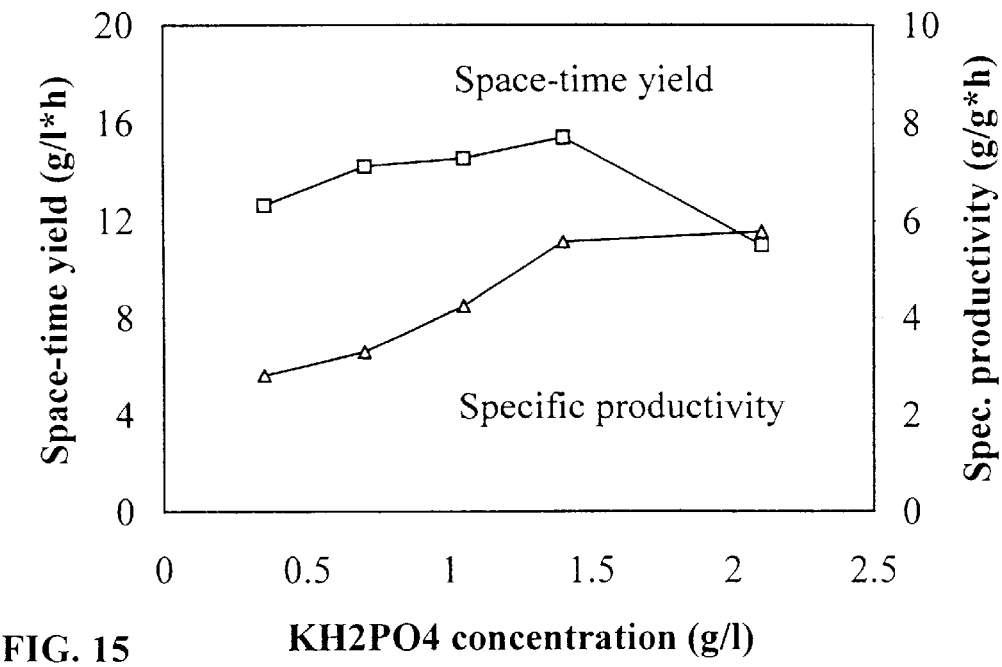

In this experiment, the maximum space-time yield was 15.43 g/(l*h), and was also achieved with 1.4 g/l $KH_2PO_4$. A space-time yield of 12.62 gI/(l*h) was measured at 0.35 g/l $KH_2PO_4$. The biomass-specific productivity increased continuously with increasing phosphorous concentration, from 2,82 g/(g*h) at 0.35 g/l $KH_2PO_4$, to 5.78 g/(g*h) at 2.1 g/l KH$_2$PO$_4$ (FIG. 15). Therefore the present experiments indicated that, for a higher biomass-specific productivity, space-time yield and product concentration for *Aureobasidium pullulans*, it should be advantageous if a higher phosphorous concentration were to be used, in contrast to the values indicated in the technical literature, where lower optimal phosphors concentrations are indicated for *Aspergillus niger*.

With a residence time of about 17 hours, (Although not plotted) the gluconic acid concentration increased to 1.05 g/l with an increasing KH$_2$PO$_4$ concentration, and then decreased at higher KH$_2$PO$_4$ concentrations. At 0.35 g/l KH$_2$PO$_4$ (which corresponds to the initial concentration), about 200 g/l of gluconic acid was continuously formed at a residence time of approximately 17 hours. At 1.05 g/l KH$_2$PO$_4$, under otherwise identical conditions, approximately 270 g/l gluconic acid was formed. No major differences in growth were observed. The highest space-time yield was achieved with 10.5 g/l KH$_2$PO$_4$ and was 15.31 g/l*h.

FIG. 14 shows the influence of phosphorous on continuous gluconic acid fermentation at a residence time of approximately 13 hours.

FIG. 15 shows the influence of phosphorous on the biomass-specific productivity and space-time yield at a residence time of approximately 13 hours.

EXAMPLE 14

Influence of Magnesium on the Continuous Fermentation of Gluconic Acid with DSM 7085.

The influence of magnesium was investigated in chemostat experiments with a residence time of approximately 20 hours. The medium was the same as in Example 10 (with 1.4 g/l KH$_2$PO$_4$, about 450 g/l glucose, 5 mM manganese, 1 mM iron, etc.).

Figure 16:
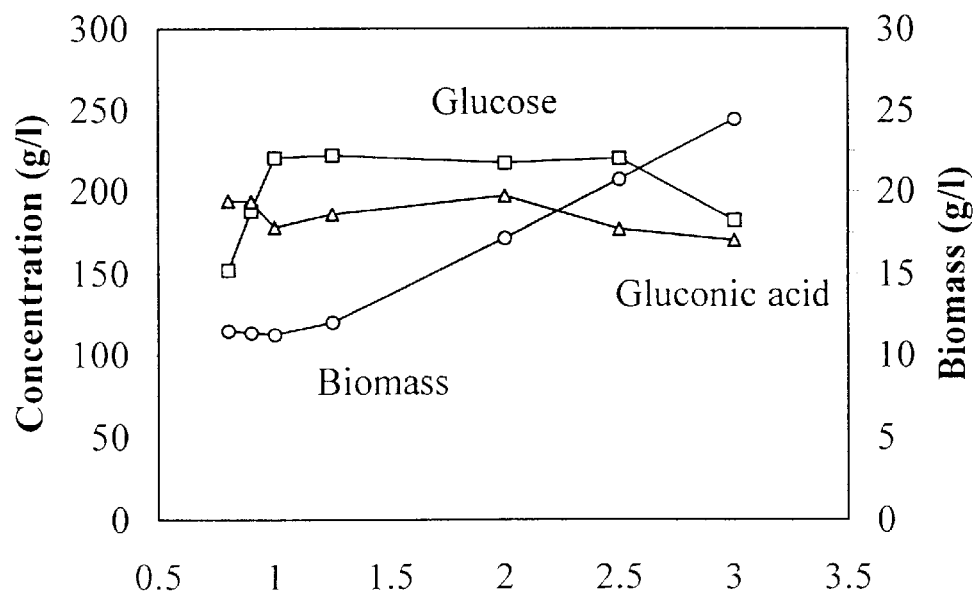
FIGS. 16 and 17 show the influence of the magnesium ion concentration and the temperature.

FIG. 16 shows the curves of the biomass, glucose and gluconic acid concentrations at various magnesium concentrations. In these experiments, a strong influence of magnesium on the growth of *Aureobasidium pullulans* was observed. The biomass remained unchanged at magnesium concentrations from 0.8 to 1 mM. But with increasing magnesium concentration from 1 mM to 3 mM magnesium, a strong continuous increase of the biomass by a factor of up to about 2.17 was observed. 11.26 g/l of biomass was formed with 1 mM magnesium, as compared to 24.45 g/l of biomass for about 3 mM magnesium (FIG. 16). With the high biomass, the dissolved oxygen concentration in the glass fermenter was insufficient for an optimum production of gluconic acid, in spite of aeration with pure oxygen.

No significant differences in the gluconic acid concentration were observed. The gluconic acid concentration increases with decreasing Mg concentration, and reaches maximum concentrations of less than about 200 g/l. The specific productivity decreases with increasing magnesium concentration. The magnesium concentration of 1.42 mM, which was used in essentially all of the other discussed experiments, is in the optimum concentration range.

The gluconic acid and glucose concentrations in FIG. 15 show a worsening of the selectivity at a magnesium concentration of more than 2 mM, which can essentially be attributed to the high biomass. Surprisingly, however, the selectivities are also very poor, even at low magnesium concentrations of less than 1 mM. According to information in the literature, low magnesium concentrations are advantageous for the synthesis of FAD, the cofactor of glucose oxidase, and thus for optimum gluconic acid production. According to the experimental results discussed above, however, low magnesium concentrations have a negative effect on product selectivity and thus on the economy of the process.

FIG. 16 shows the influence of magnesium on continuous gluconic acid fermentation.

EXAMPLE 15

Influence of Temperature on Continuous Gluconic Acid Fermentation with DSM 7085

The influence of the temperature on the continuous forrrmation of gluconic acid with *Aureobasidium pullulans* DSM 7085 was investigated in chemostat experiments with a residence time of approximately 12–13 hours with a medium defined as in Example 10, but with 1 mM iron, 1.4 g/l KH$_2$PO$_4$ and about 360 g/l glucose.

All the preceding tests were performed at 30° C. The organisms, however, are also capable of growth and production at lower temperatures. Different optimum temperatures were determined for growth and production.

Figure 17:
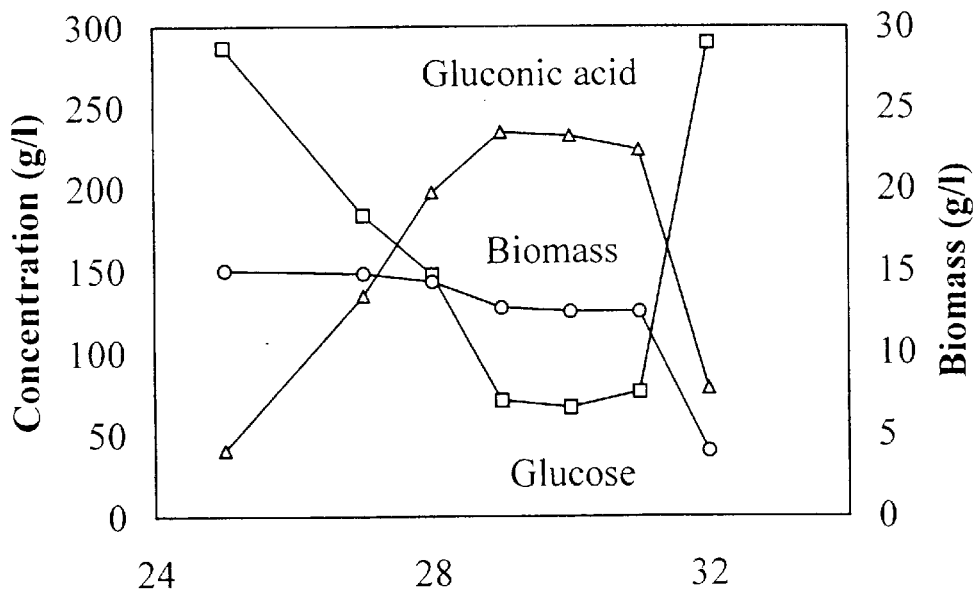

FIG. 17 shows the curves of biomass, glucose and gluconic acid concentration as a function of the temperature. A continuous increase of the biomass concentration with decreasing temperature was observed. For example, the biomass at about 31° C. and about 30° C. was 12.45 g/l, and at around 27° C. it was 14.8 g/l. An increase in temperature by only one degree C. (from 31° C. to 32° C.) essentially caused a drastic reduction of the biomass concentration. The highest product concentrations were achieved at temperatures between 29° C. and 31° C. 234.53 g/l gluconic acid was continuously formed at 29° C., 232.19 g/l at 30° C. and 223.5 g/l at 31° C. At 32° C., the production concentration deceased drastically, and in the steady state it was only 78.09 g/l. A continuous reduction of the product concentration was observed at temperatures below about 29° C. (FIG. 17). The glucose concentration in the fermenter was between 66.21 g/l at 30° C. and 290.13 g/l at 32° C. The maximum space-time yield and biomass-specific productivity were achieved at a temperature of around 29° C. to about 30° C.

FIG. 17 shows the influence of temperature on the continuous gluconic acid fermentation with a residence time of approximately 12 hours.

Fed-Batch Fermentation

Figure 18:
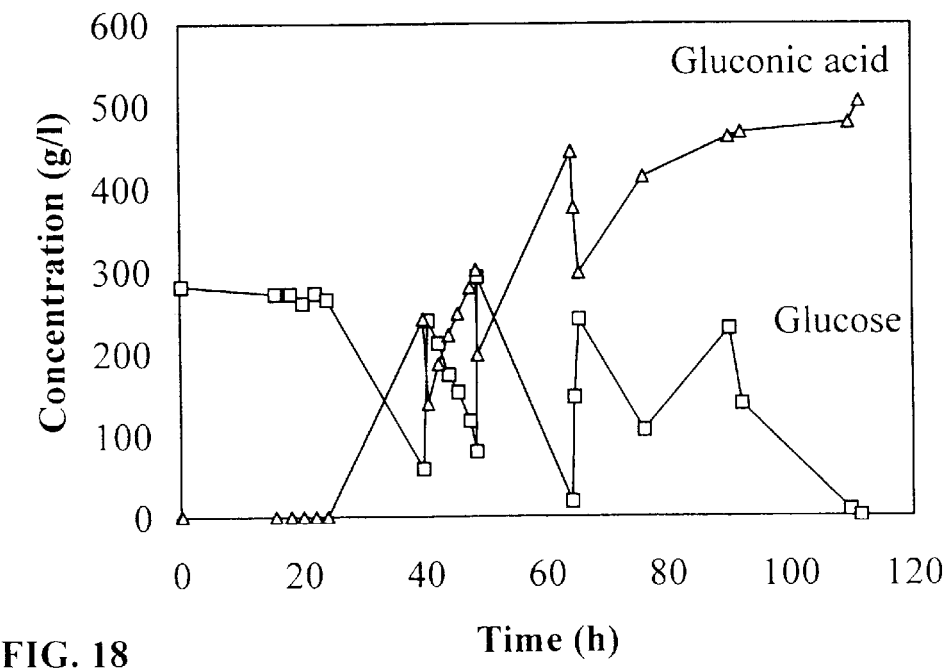
FIG. 18 shows curves for a fed-batch experiment.

In a fed-batch experiment, a maximum gluconic acid concentration of about 504 g/l was achieved. The glucose was completely converted (FIG. 18). The delay in the increase of the gluconic acid concentration above about 450 g/l was due to technical problems (e.g. dilution effects, substrate addition). FIG. 18 shows the fed-batch gluconic acid fermentation with *Auerobasidium pullulans*.

EXAMPLE 16

Process Optimization of Continuous Gluconic Acid Fermentation.

16.1 Continuous Gluconic Acid Fermentation Under Optimized Conditions.

With the optimized medium (as in Example 10, but with 1 mM iron, 1.4 g/l KH$_2$PO$_4$ and about 450 g/l glucose), about 315 g/l of gluconic acid was formed continuously in the agitator vessel (3 l) with a pH of around 6.5, oxygen saturation of approximately 0.55%, temperature of about 30° C. with a residence time of about 21 hours. About 330 g/l gluconic acid was produced with a residence time of about 25 hours. In the steady state, the biomass was about 6.8 g/l.

The gluconic acid concentration can be maximized by extending the residence time and with higher glucose concentrations. At gluconic acid concentrations of more than about 300 g/l, however, there is a severe inhibition of product.

16.2 Continuous Gluconic Acid Fermentation with Biomass Retention by Means of Microfiltration.

A good alternative for the acceleration of the maximization of the product concentration is the partial retention of biomass by means of microfiltration (cross over filtration). The biomass retention by means of microfiltration makes it possible to break the link between growth and the residence time. It also makes it possible to perform the process at high oxygen concentrations which are toxic for growth, whereby the highest specific productivities are also achieved. With a residence time of approximately 23 hours, an oxygen saturation of about 290%, and with about 23 g/l accumulated biomass (approximately 80% microfiltrate portion), about 375 g/l gluconic acid was formed continuously with complete conversion. With a residence time of about 19 hours and a biomass of about 25 g/l, about 370 g/l of gluconic acid were also produced continuously with complete conversion (glucose undetectable). Based on the results indicated above, it seems possible to shorten the residence time.

16.3 Cascading of two fermenters.

An additional alternative process method is the cascading of two or more fermenters. This makes possible a distribution of the residence time, whereby different optima can be set, for example, for growth and production, independently of one another. In a test series, two agitator vessel fermenters were used with a total working volume of approximately 4.5 liters. A medium analogous to Example 9 was used but with about 450 or about 600 g/l glucose, 1 mM Fe, 5 mM Mn, 1.4 g/l $KH_2PO_4$.

The first fermenter was operated with an oxygen saturation between about 120% to about 180% and the second fermenter with more than about 300%.

The residence time in the first stage was approximately 22 hours, and in the second stage a total of about 37 hours. The objective in the first stage was to achieve a maximum space-time yield for a conversion of more than about 60%, as well as rapid growth, and in the second stage the objective was to achieve the maximum gluconic acid concentration. About 366 g/l gluconic acid and a biomass of about 5.3 g/l were measured in the first fermenter, and about 433 g/l gluconic acid and a biomass of about 7.8 g/l were measured in the second, in the test with about 600 g/l glucose.

In the test with about 450 g/l glucose and a residence time of about 22 hours, measurements made in the first fermenter indicated about 305 g/l gluconic acid, about 5.9 g/l biomass and about 70 g/l glucose. In the second fermenter, about 350 g/l gluconic acid and about 8.1 g/l biomass were measured after a total residence time of about 38 hours and complete conversion.

With an additional shortening of the residence times, about 272 g/l gluconic acid was formed continuously in the first stage at about 19.5 hours, and with a total residence time of 30.8 hours, about 370 g/l gluconic acid was formed in the second stage.

One feature of the invention resides broadly in the process for the production of gluconic acid by fermentation in aqueous liquid containing sugar, characterized by the fact that the process is conducted:

with a phylum of Aureobasidium pullulans (de bary) Arnaud forming gluconic acid in continuous culture from glucose greater than or equal to 200 g/l at greater than or equal to 90% yield conversion and greater than or equal to 90% molar selectivity is used; though strains are most favored which are able to produce gluconilc acid with a molar selectivity of ≧95%.

in a medium containing optimum concentrations of Fe and Mn, with an N-dependent iron and/or manganese ion concentration in the feed, which with an N-concentration corresponding to 3 g/l $NH_4Cl$ is greater than or equal to 0.5 mM (Fe) and greater than or equal to 0.5 mM (Mn);

at pH values from 4.5 to 8, and at temperatures of 24 to 32° C.

Another feature of the invention resides broadly in the process, characterized by the fact that a phylum isolated from wildflowers, in particular from their blooms and stems, is used.

Yet another feature of the invention resides broadly in the process, characterized by the fact that an *Aureobasidiuim pullulans* (de bary) Arnaud having the Registration Numbers DSM 7085, DSM 7086, DSM 7087 or DSM 7088 is used.

Still another feature of the invention resides broadly in the process, characterized by the fact that the process is conducted at a pH between 6.0 and 7 and at a temperature of 29–31° C.

Yet still another feature of the invention resides broadly in the process, characterized by the fact that the process is conducted with iron, manganese and magnesium concentrations in the feed, as a function of N, which are 0.5–3 mM Fe, 2.5–5 mM Mn) and 1–2 mM (Mg) respectively at an N concentration of 3 g/l $NH_4Cl$.

Another feature of the invention resides broadly in the process, characterized by the fact that greater than or equal to 0.7 g/l $KH_2PO_4$ is provided in the feed.

Still another feature of the invention resides broadly in the process, characterized by the fact that the fermentation is performed continuously with residence times of 10–40 hours.

Still yet another feature of the invention resides broadly in the process, characterized by the fact that the process is conducted with an oxygen saturation which increases with increasing residence time, whereby values of the oxygen saturation are selected for 13 h residence time between 80 and 150%, in particular 120%.

Another feature of the invention resides broadly in the process, characterized by the fact that the process is performed with unsupported microorganisms (not on a carrier) and with biomass retention.

Yet another feature of the invention resides broadly in the process, characterized by the fact that the process is conducted in at least two fermenters connected in cascade.

Still another feature of the invention resides broadly in the process, characterized by the fact that the process is conducted in a first silage with 120–170% oxygen saturation and residence times of 10–25 hours, in particular 12–18 hours, and in the second stage with greater than 360% oxygen saturation and a total residence time greater than or equal to 15 hours, in particular 18–30 hours.

Another feature of the invention resides broadly in the process, characterized by the fact that the fermentation is performed with glucose feed concentrations of 300–600 g/l.

Yet still another feature of the invention resides broadly in the process, characterized by the fact that the fermentation is performed in a fluidized bed reactor with immobilized biomass.

Still another feature of the invention resides broadly in the *Aureobasidium pullulans* (de bary) Arnaud strains isolated from wildflowers by cultivation under acid conditions with increased glucose concentration and good oxygen supply.

Another feature of the invention resides broadly in the *Aureobasidium pullulans* (de bary) Arnaud strains isolated from incubation charges of comminuted blooms and stems of central European wildflowers gathered from spring to summer, in citric acid solution at pH 2.5 with 100 g/l glucose, with the addition of wetting agent and a sufficient oxygen supply provided by shaking.

Still another feature of the invention resides broadly in the *Aureobasidium pullulans* (de bary) Arnaud strains DSM 7085, DSM 7086, DSM 7087 and DSM 7088.

All, or substantially all, of the components and methods of the various embodiments may be used with at least one embodiment or all of the embodiments, if any, described herein.

The details in the patents, patent applications and publications may be considered to be incorporable, at applicant's option, into the claims during prosecution as further limitations in the claims to patentably distinguish any amended claims from any applied prior art.

The appended drawings, in their entirety, including all dimensions, proportions and/or shapes in at least one embodiment of this intention, are, if applicable, accurate and to scale and are hereby incorporated by reference into this specification.

The invention as described hereinabove in the context of the preferred embodiments is not to be taken as limited to all of the provided details thereof, since modifications and variations thereof may be made without departing from the spirit and scope of the invention.

EXAMPLE 17

In a further experiment gluconic acid was produced continuously using a fermentation medium similar to example 4 but half-concentrated and with 360 g/l glucose; 1.5 g/l $NH_4Cl$; 0.5 mg/l $ZnSO_4$—6 aq; 0.5 mg/l $CuSO_4$—5 aq; 2.5 2.5 mM Mn; 1 mM Fe; 1 mM Mg and 1.4 g/l $KH_2PO_4$. In a continuous fermentation without retention of biomass (3.9 g/l biomass in steady state) at 29–30° C., pH 6.5 and a residence time of 21 h, a gluconic acid concentration of 305 g/l was obtained with molar selectivity >98≈and a glucose conversion >95%.

What is claimed is:

1. A process for production of gluconic acid by fermentation in liquid growth medium comprising sugar, said process comprising;

introducing a strain of *Aureobasidium pullulans* (de bary) Arnaud to said growth medium for said fermentation, wherein said medium contains iron and manganese ions at concentrations that result in production of gluconic acid at concentrations of greater than or equal to 230 g/L within said medium, said concentrations of iron and mangenese ions being at least 0.5 mM, and contacting said fermentation to produce gluconic acid at a concentration of greater than or equal to 230 g/L within said growth medium; and said recovering said gluconic acid from the growth medium.

2. A process for production of gluconic acid by fermentation in liquid media comprising sugar, said process comprising;

selecting a strain of *Aureobasidium pullulans* (de bary) Arnaud, wherein said strain being selected is able to convert glucose to gluconic acid in a culture resulting in a concentration of gluconic acid of at least 200 g/l, with a conversion of at least 90%, and with a molar selectivity of at least 90%;

adding said strain to a fermentation medium containing iron ions at a concentration of at least 0.5 mM, manganese ion concentration of at least 0.5 mM and a nitrogen concentration corresponding to an ammonium salt concentration between about 0.3–9.0 g/L;

conducting said fermentation at a pH between about 4.5 and about 8 and at a temperature between about 24° C. and about 32° C., wherein said process results in production of gluconic acid at concentrations greater than or equal to 200 g/L within said medium; and recovering said gluconic acid from the growth medium.

3. The process according to claim 2, wherein the strain comprises a strain isolated from wildflowers.

4. The process according to claim 3, wherein the strain of *Aureobasidium pullulans* (de bary) Arnaud comprises at least one strain having one of the following registration numbers: DSM 7085, DSM 7086, DSM 7087 and DSM 7088.

5. The process according to claim 2 wherein the process is conducted at a pH between 6.0 and 7 and at a temperature in the range of 29–31° C.

6. The process according to claim 2, wherein to said medium is added a feed containing an iron ion concentration in the range of 0.5–3 mM, a manganese ion concentration in the range of 2.5–5 mM, a magnesium ion concentration in the range of 1–2 mM and an ammonium salt concentration of about 3 g/L.

7. The process according to claim 6, wherein greater than or equal to 0.7 g/l $KH_2PO_4$ is provided in said feed.

8. The process according to claim 2, wherein the fermentation is performed continuously with residence times in the range of 10–40 hours.

9. The process according to claim 2, wherein the process is conducted with an oxygen saturation which increases with increasing residence time, whereby values of the oxygen saturation are between 80 and 150% and are selected for a residence time between 5 and 100 hours.

10. The process according to claimed 8, wherein said microorganism is retained with a filter in said medium as a biomass.

11. The process according to claim 9, wherein the process is conducted in at least two fermenters connected in cascade.

12. The process according to claim 11, wherein the process is conducted in a first stage with 120–170% oxygen saturation and residence times of 10–25 hours, and in the second stage with greater than 360% coxygen saturation and a total residence time greater than or equal to 15 hours.

13. The process according to claim 8, wherein the fermentation is performed with glucose feed concentrations of 300–600 g/l.

14. The process according to claim 13, wherein the fermentation is performed in a fluidized bed reactor and said strain of *Aureobasidium pullulans* is immobilized on a support.

15. The process according to claim 3, wherein the strain comprises a strain isolated from blooms and stems of said wildflowers.

16. The process according to claim 6 wherein said ammonium salt is $NH_4Cl$.

17. The process according to claim 2 wherein said nitrogen concentration is from an organic source.

18. The process according to claim 2 wherein said nitrogen concentration is from amino acids.

19. The process according to claim 9, wherein said oxygen saturation is approximately 120%.

20. The process according to claim 11, wherein said residence time of said first stage is between approximately 12–16 hours.

21. The process according to claim 11, wherein said residence time of said second stage is between approximately 18–30 hours.

* * * * *